United States Patent [19]
Tobin et al.

[11] Patent Number: 5,131,265
[45] Date of Patent: Jul. 21, 1992

[54] REAL-TIME RHEOLOGY MEASUREMENT SENSOR

[75] Inventors: James R. Tobin, Clearwater; Robert W. Pennisi, Boca Raton; Frank Starsky, Coral Springs, all of Fla.

[73] Assignee: Motorola, Inc., Schaumburg, Ill.

[21] Appl. No.: 658,809

[22] Filed: Feb. 22, 1991

[51] Int. Cl.⁵ .................. G01N 11/00; G01N 11/10
[52] U.S. Cl. .................. 73/54.23; 73/54.01; 73/861.74
[58] Field of Search .......... 73/59, 54, 861.74, 861.71; 137/92

[56] References Cited

U.S. PATENT DOCUMENTS

| | | | |
|---|---|---|---|
| 2,943,486 | 7/1960 | Osgood | 73/861.74 |
| 3,147,612 | 9/1964 | Evans | 73/59 |
| 3,147,620 | 9/1964 | Stapler | 73/861.74 |

FOREIGN PATENT DOCUMENTS 1110891  7/1961  Fed. Rep. of Germany ... 73/861.74

Primary Examiner—Hezron E. Williams
Assistant Examiner—Michael J. Brock
Attorney, Agent, or Firm—Daniel K. Nichols; Dale W. Dorinski

[57] ABSTRACT

A sensor (18) for measuring the rheology of materials is provided, comprising a deformable beam (20) simply supported at two locations (21 and 22). The beam has supported and unsupported portions, with the unsupported portion (28) extending beyond the supported portion. A strain gauge (23) is attached to the supported portion of the deformable beam (20), and measures the induced strain on the beam when the unsupported portion (28) is deflected by a moving material.

16 Claims, 5 Drawing Sheets

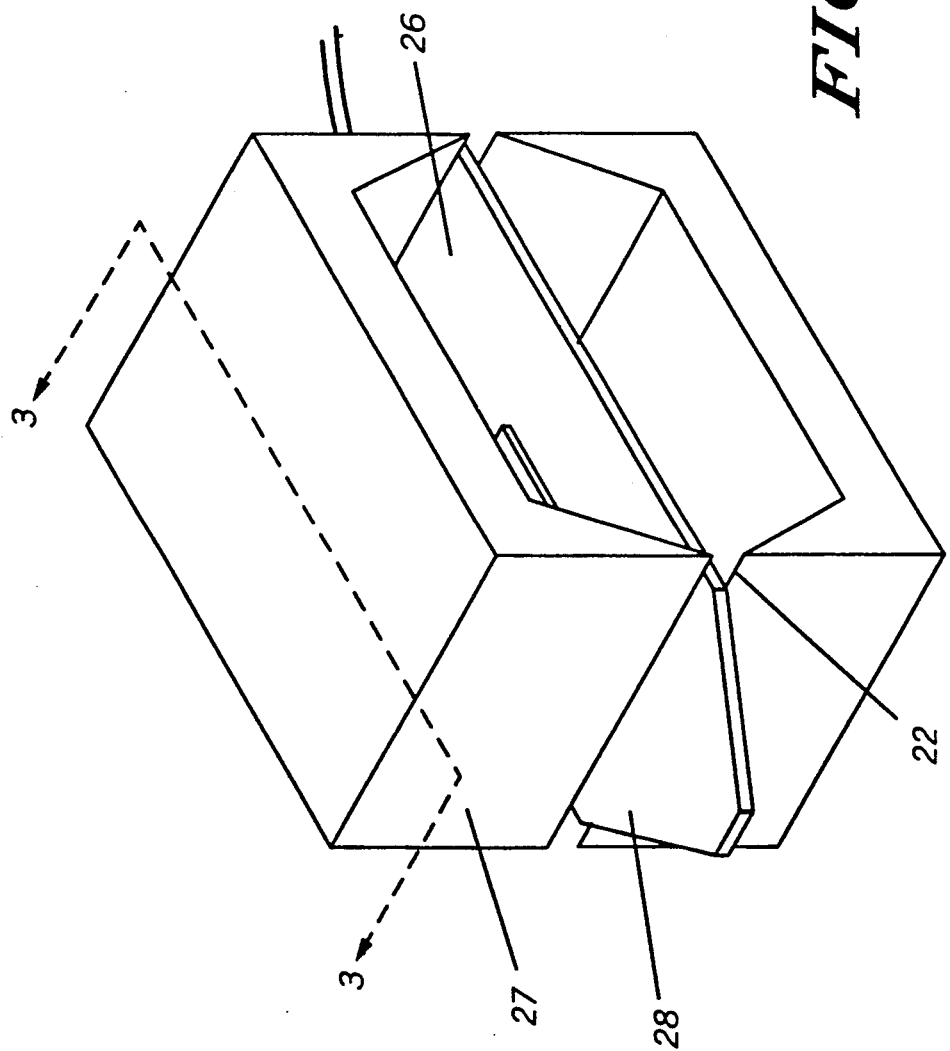

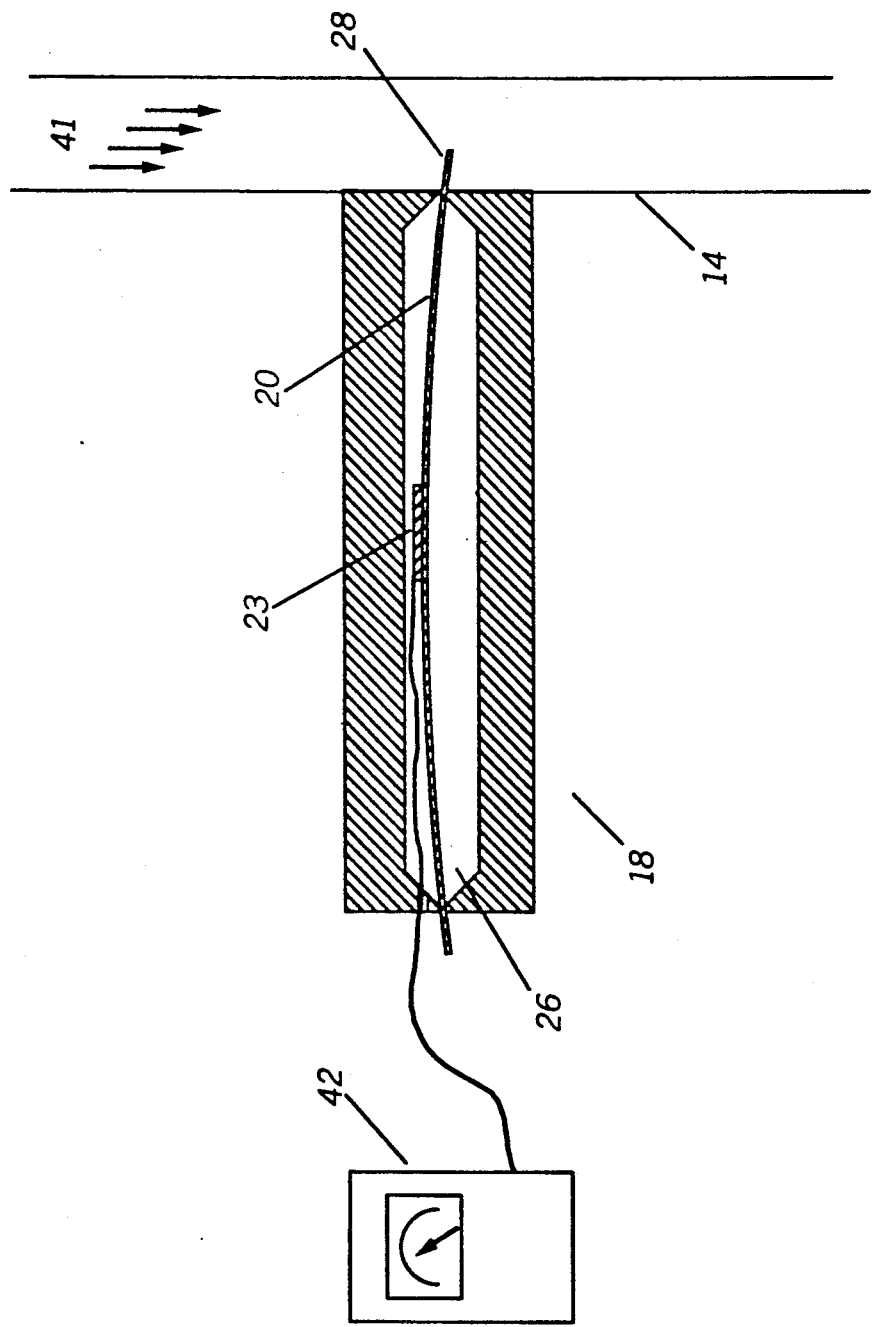

REAL-TIME RHEOLOGY MEASUREMENT SENSOR

TECHNICAL FIELD

This invention relates generally to sensing devices, and more specifically to a sensor to measure the rheological properties of materials.

BACKGROUND

Injection molding and transfer molding processes are commonly used in the manufacture of plastic articles. In both of these processes, the operation begins with the loading of a solid resin into a molding machine. The resin is heated and melted under pressure and the hot liquid resin is transferred from a reservoir to the mold cavities. When the resin cools, the part is ejected from The mold. In transfer molding, a reactive resin is used and a thermoplastic resin is used with injection molding. Molding presses for these processes consist of a preheater, a hydraulic power unit, a platen, a multi-cavity mold, and a control unit for controlling the process. The transfer molding resin is in the form of a pellet and is placed into the preheater. After the resin has reached the desired temperature, a plunger compresses the pellet and maintains the forcing pressure for ten to fifty seconds, depending upon the mold temperature and the type of resin. Once the resin has softened to a workable viscosity range, the plunger transfers the resin into the mold cavity via runners and gates. This transfer is completed within a few seconds. Once the resin has been forced into the mold cavity, the resin reacts or cures to form a thermoset material, the cavity is then opened, and the solid part is ejected.

The injection molding process is similar to transfer molding except that a continuous supply of resin is provided to a heated feed screw that heats and pressurizes the resin, converting it into a molten state. The feed screw rapidly transfers the molten resin under pressure into the mold cavity where the resin quickly cools and solidifies. The mold cavity is then opened and the finished part is ejected.

In both these processes, the rheology of the molten resin is critical to the outcome of the molded part. If the resin is not heated properly prior to injection, the mold cavity will not fill because the resin viscosity is too high. Conversely, if the resin is overheated prior to injection, degradation of the thermoplastic polymer or premature curing of the reactive resin will occur.

Conventional methods of monitoring the rheology of materials are cumbersome and require several types of information. For example, the flat-plate orifice method requires knowledge of the relative orifice sizes, the fluid velocity past the orifice, and the pressure of the system on both sides of the orifice. Other methods of monitoring the material rheology are performed in an indirect manner. Micromet Instruments, Inc. of Cambridge, Mass. produces a sensor that measures the ionic viscosity of a material by measuring the relative amount of ionic species in a material, which gives inferential information about the chemical structure of a polymer. As a thermoset polymer reacts, the mobility of ionic species decreases with the subsequent increase in solution viscosity. This type of measurement does not directly measure the rheological property of a material, but provides inferential information about the properties. Other test methods require that samples of finished parts be removed from the mold and submitted to an off-line test where melt flow rate and other physical properties of the molded plastic may be determined. One example of an off-line measurement system is the Tinius-Olsen extrusion plastometer, made by Testing Machine Company of Willow Grove, Pa. Once this is known, molding parameters such as temperature, time, and pressure are then closely controlled in an attempt to achieve uniformity. It is clear that this type of off-line measurement of the resin properties does not yield real-time information and can only be performed on a batch basis, requiring the destruction of at least part of the molded product. A method of determining the viscosity and rheology of the molten plastic during the molding operation would be extremely beneficial to controlling and monitoring the quality of a continuous molding operation.

SUMMARY OF THE INVENTION

Briefly, according to the invention, there is provided a sensor for measuring the rheology of materials, comprising a deformable beam simply supported at two locations. The beam has supported and unsupported portions, with the unsupported portion extending beyond the supported portion. A strain gauge is attached to the supported portion of the deformable beam, and measures the induced strain on the beam when the unsupported portion is deflected by a moving material.

BRIEF DESCRIPTION OF THE DRAWINGS

FIG. 2b is an isometric view of the assembled sensor.

FIG. 4 is a cross-sectional view of the sensor during operation.

DETAILED DESCRIPTION OF THE PREFERRED EMBODIMENT

Figure 1:
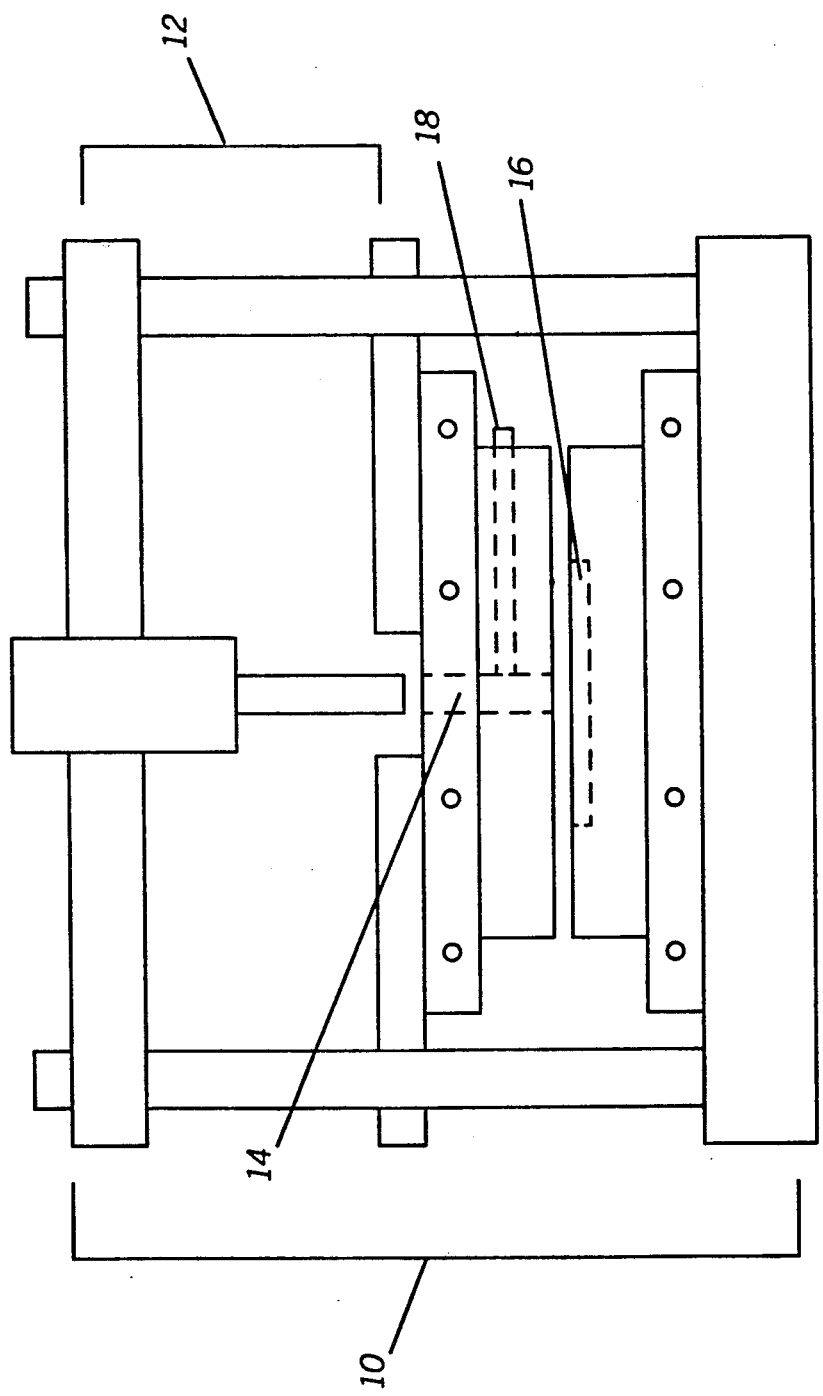
FIG. 1 is a block diagram of a molding machine and rheology sensor.

Referring to FIG. 1, a molding machine 10 consists of an injector portion 12 which feeds heated resin through a transfer port 14 via a hydraulic ram or screw feed system into heated mold cavity 16. A rheology measuring sensor 18 is fitted into the channel 14 between the injector portion and the mold cavity. As the heated resin is injected into the cavity and forced through the transfer area 14, the sensor 18 measures the rheology of the heated resin.

Figure 2A:
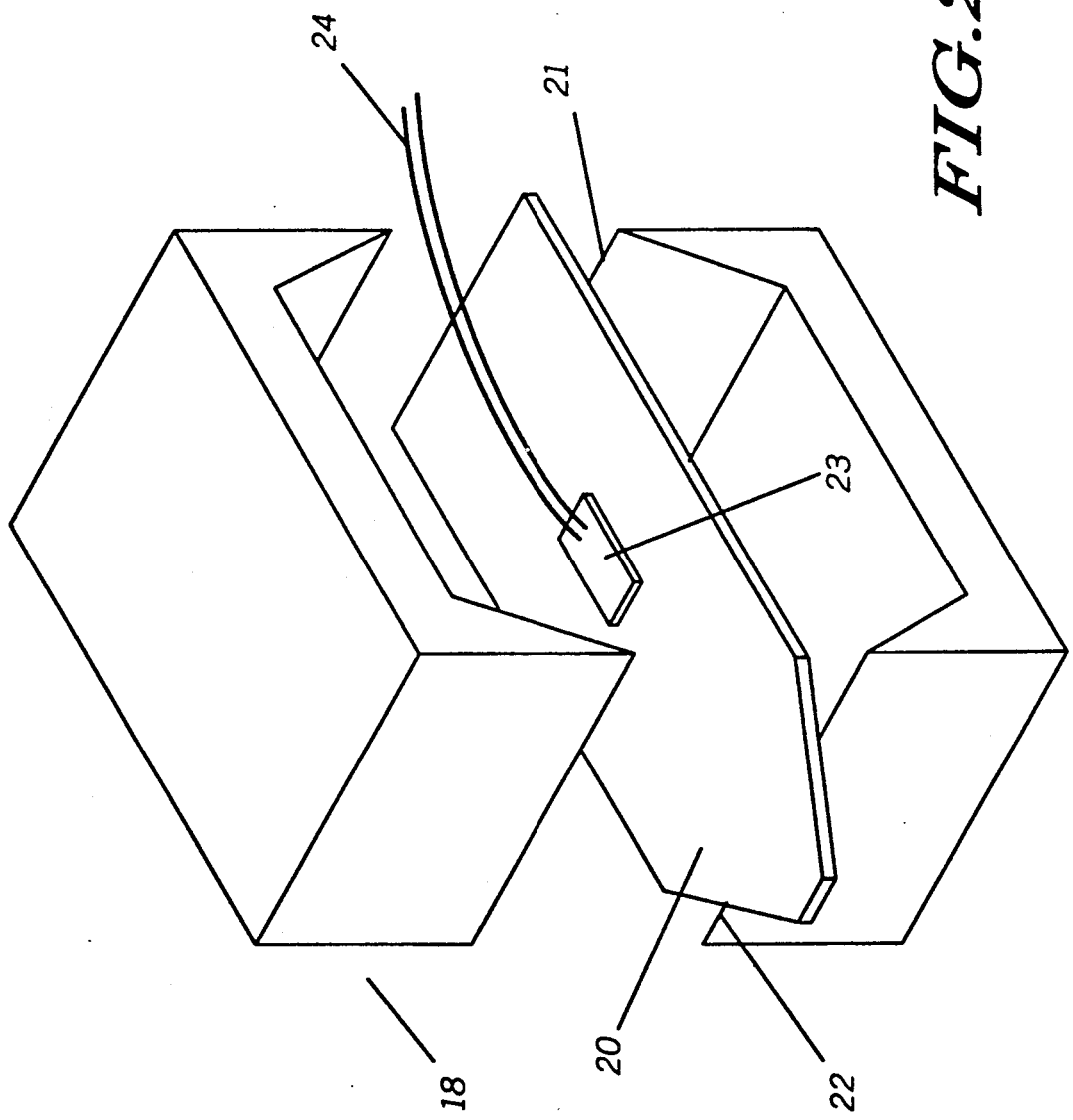
FIG. 2a is an exploded isometric view of the sensor in accordance with the present invention.

Referring now to FIG. 2a, a rheology measurement sensor 18 consists of a deformable metal or polymer beam 20 which is simply supported at two points (21 and 22). Depending upon the type of material being measured, the deformable beam may be made from metals such as nickel, stainless steel, copper, brass or other alloys, or from polymeric resins such as high temperature engineering thermoplastics like polysulfone, polyetheretherketone, polyimide, polyester, polyamide and other similar resins if the materials to be measured are corrosive to conventional metal systems. A simply supported beam, as referred to hereinafter, is designated to mean that the beam is clamped on both top and bottom using a knife edge type of apparatus so that only a very small portion of the beam is held rigidly between the clamps. The beam 20 is clamped at one end 21 and at a short distance from the opposite end 22. A strain gauge 23 is mounted at the approximate midpoint of the beam between the two support edges. The strain gauge 23 serves to measure the deflection of the beam as the moving material deflects the sensor. The output of the strain gauge 23 is via wires 24 led to an external measuring device (not shown). A second strain gauge may optionally be mounted on the other side of the beam directly opposite the first strain gauge 23. Output wires 24 are also used on the second strain gauge.

When the sensor is assembled (FIG. 2b), the beam is held in a cavity 26 created by the mounting and clamping sites and typically machined from a block of metal 27. A portion of the beam 28 extending beyond the supported portion of the beam 22 is designed to be deflected by the heated resin in the injection molding operation.

Figure 3:
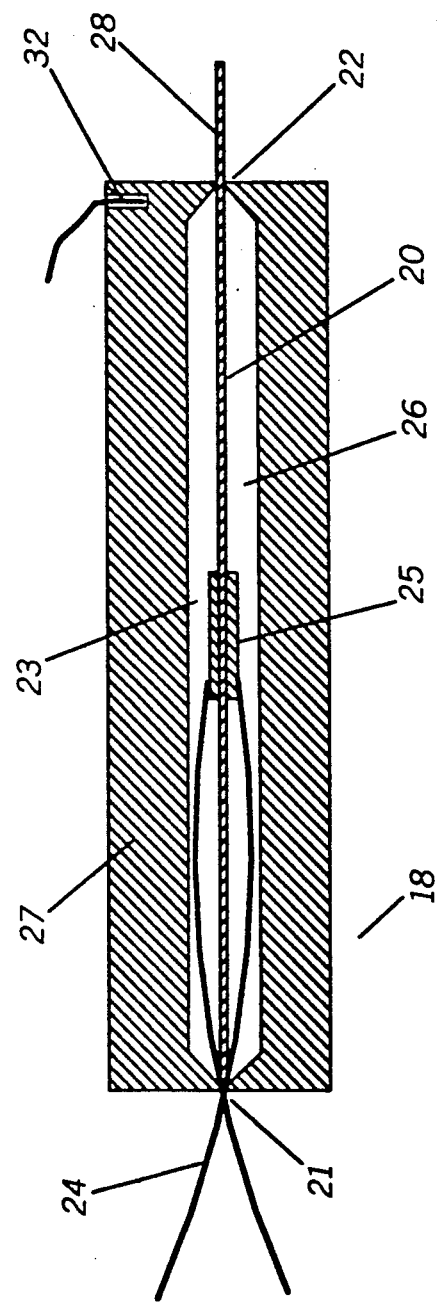
FIG. 3 is a cross-sectional view of the sensor of FIG. 2 through section 3—3.

In order to provide the reader with a clearer understanding of the composition of the rheology sensor, a cross-sectional view of FIG. 2b through section 3—3 is shown in FIG. 3. The beam 20 is simply supported at points 21 and 22 in a single line. Strain gauge 23 is mounted in the center of the beam midway between the two support points and the unsupported portion 28 is the portion intended to be deflected by the moving material. The configuration of area 28 may be rectangular, triangular, semicircular or other shapes as desired for the particular application. A thermocouple 32 may be mounted in the sensor in order to aid in the characterization of the material rheology. The thermocouple 32 is mounted near the unsupported portion of the beam, preferably in an area that will not obstruct the flow of material past the unsupported beam portion, but also provide accurate temperature readings of the material.

During the molding process, material flow causes the beam in the sensor to deform, as shown in FIG. 4. The sensor 18 is mounted in the transfer portion 14 of the molding machine such that the unsupported portion 28 is directly perpendicular to the material flow in the transfer area 14. As the molten resin 41 flows past the unsupported portion 28 of the sensor, in this case in a downward direction, the extended portion of the sensor 28 is deflected downward causing the center of the beam 20 to be deflected in the opposite direction. As this deflection occurs, the strain gauge 23 measures the elongation of the upper surface of the beam 20. The induced strain is measured by a meter 42 which allows one to correlate rheological properties of the material 41. Note that cavity 26 inside the sensor must be large enough to allow full deflection of the beam 20. If desired, a second strain gauge identical to strain gauge 23 may optionally be mounted on the opposite side of beam 20, directly opposite strain gauge 23, and used to increase the accuracy of the measurement. After the molten material flows pass the sensor and into the cavity, the molding cycle is complete and the cavity is opened to release the part.

In the preferred embodiment of a sensor made to be used in a transfer molding machine, the deformable beam is a thin stainless steel sheet 2.375 inches long × 0.25 inches wide × 0.062 inches thick. The support points are 2.125 inches apart, and the width of the unsupported portion in the moving material stream is 0.25 inches and shaped in a triangular shape. Additionally semicircular or rectangular shapes can be utilized. The housing for the deformable beam is made from two pieces of 3/16 inch steel plate. Two strain gauges (fully encapsulated K alloy strain gauges, Catalog number WK-06-062AQ-500 from Measurements Group, Inc, Raleigh, N.C.) are adhesively mounted on opposite sides of the beam. Other strain gauges may also be used if the temperature range of the gauge is matched to the expected operating temperature of the sensor. Each strain gauge forms one leg of a wheatstone bridge analyzer made by the same company.

The examples shown in FIGS. 1–4, while illustrative, are not meant to be considered limiting and other configurations and applications of the rheology sensor may be envisioned to fall within the scope of the invention. For example, a modification of the sensor for use in measuring the rheology of solder paste can be made by configuring the unsupported portion of the beam into a stiff rod, and deflecting the rod with the moving stream of solder paste. Such a sensor will provide valuable information on the condition and printability of solder paste used in the manufacture of electronic printed circuit assemblies used in, for example, two way radios and other communication equipment.

The use of a rheology measurement sensor as described herein allows real-time determination of the rheological properties of materials. This information can be used to determine viscosity and other fundamental material properties of a molten resin during transfer molding or injection molding operations, previously unobtainable by conventional methods.

What is claimed is:

1. A sensor for measuring the rheology of materials, comprising:
    a deformable beam having supported and unsupported portions, and being simply supported at two locations, said unsupported portion extending beyond said supported portion, said unsupported portion being subject to deflection by said material in accordance with the rheology of said material; and a strain gauge attached to said supported portion of said deformable beam.

2. The sensor as described in claim 1, wherein the strain gauge is attached to the deformable beam at a location approximately midway between the two supported locations.

3. The sensor as described in claim 2, wherein another strain gauge is mounted on another side of the deformable beam substantially opposite the first strain gauge.

4. The sensor as described in claim 1, wherein the unsupported portion is mounted approximately perpendicular to and projecting into a path of the material.

5. The sensor as described in claim 1, wherein the unsupported portion is substantially triangular.

6. The sensor as described in claim 1, wherein the unsupported portion is substantially rectangular.

7. The sensor as described in claim 1, wherein the unsupported portion is substantially semicircular.

8. The sensor as described in claim 1, wherein the deformable beam is polymeric resin.

9. A sensor for measuring the rheology of plastic molding material, comprising:
    a deformable metal beam having supported and unsupported portions, and being simply supported at two locations, and having the unsupported portion extending beyond the supported portion, the unsupported portion being deflectable by the flow of the plastic molding material; and
    a strain gauge attached to the deformable beam at a location approximately midway between the two supported locations.

10. The sensor as described in claim 9, wherein a second strain gauge is mounted on a second side of the deformable metal beam substantially opposite the first strain gauge.

11. The sensor as described in claim 9, further comprising a thermocouple to measure the temperature of the plastic molding material.

12. A rheology measurement system, comprising:

a sensor comprising a deformable metal beam having supported and unsupported portions, the deformable metal beam being simply supported at two locations and having the unsupported portion extending beyond the supported portion; and a strain gauge attached to the deformable metal beam at a location approximately midway between the two supported locations; the sensor being mounted such that the unsupported portion is deflectable by the flow of a moving material; and at least one meter connected to the strain gauge for measuring the strain gauge output.

13. The sensor as described in claim 12, wherein the unsupported portion is substantially triangular.

14. The sensor as described in claim 12, wherein the unsupported portion is substantially rectangular.

15. The sensor as described in claim 12, wherein the unsupported portion is substantially semicircular.

16. The sensor as described in claim 12, further comprising a thermocouple to measure the temperature of the plastic molding material.

* * * * *